United States Patent
Theron

(10) Patent No.: US 7,172,621 B2
(45) Date of Patent: Feb. 6, 2007

(54) METHOD OF PERFORMING PROTECTED ANGIOPLASTY AND STENTING AT A CAROTID BIFURCATION

(76) Inventor: Laurence Theron, 6, rue Presbytere, Fleury sur Orne (FR) 14123

( * ) Notice: Subject to any disclaimer, the term of this patent is extended or adjusted under 35 U.S.C. 154(b) by 200 days.

(21) Appl. No.: 10/950,179

(22) Filed: Sep. 24, 2004

(65) Prior Publication Data
US 2006/0074474 A1    Apr. 6, 2006

(51) Int. Cl.
A61F 2/06 (2006.01)
A61F 2/01 (2006.01)
A61M 29/00 (2006.01)

(52) U.S. Cl. ................. 623/1.11; 623/1.12; 606/200

(58) Field of Classification Search ........... 623/1.11, 623/1.1, 1.2, 1.21, 1.23; 606/190, 194, 192, 606/200; 600/207; 604/96.01, 101.04, 101.01, 604/102.02, 102.03, 103.04
See application file for complete search history.

(56) References Cited
U.S. PATENT DOCUMENTS 5,800,525 A * 9/1998 Bachinski et al. ........... 623/1.1
6,645,220 B1 * 11/2003 Huter et al. ................. 606/200
2004/0015184 A1 * 1/2004 Boyle et al. ................. 606/200

* cited by examiner

Primary Examiner—Anhtuan T. Nguyen
Assistant Examiner—Amanda Adams
(74) Attorney, Agent, or Firm—James J. Leary

(57) ABSTRACT

A method is described for performing protected angioplasty and stenting of a patient's carotid bifurcation. A self-expanding stent is deployed across a stenosis in the patient's carotid artery. A catheter system that includes a rapid exchange balloon angioplasty catheter with an occlusion balloon catheter positioned through the guidewire lumen is advanced through the guiding catheter and into the distal end of the stent. The occlusion balloon is inflated within the lumen of the stent to occlude the carotid artery and to prevent any embolic debris from traveling downstream from the treatment site. The angioplasty balloon is inflated to dilate the stenosis and to complete the expansion of the self-expanding stent. The angioplasty catheter is withdrawn and any potential embolic debris is aspirated out through the lumen of the guiding catheter. The occlusion balloon is deflated and the catheter system is withdrawn.

10 Claims, 13 Drawing Sheets

METHOD OF PERFORMING PROTECTED ANGIOPLASTY AND STENTING AT A CAROTID BIFURCATION

FIELD OF THE INVENTION

The present invention relates generally to catheter based treatments for vascular disease. More particularly, it relates to an improved method of performing angioplasty and stenting utilizing embolic protection to capture any potential embolic debris. The method is particularly applicable for treatment of vascular disease at a carotid bifurcation.

BACKGROUND OF THE INVENTION

Catheter based treatments, including angioplasty and stenting, represent a tremendous advancement in the treatment of obstructive vascular disease. Percutaneous transluminal angioplasty (PTA) of stenotic lesions in peripheral arteries using a balloon dilatation catheter was first reported by Gruentzig et al in 1974 (Percutaneous recanalization after chronic arterial occlusion with a new dilator-catheter modification of the Dotter technique; Dtsch Med Wochenschr Dec. 6, 1974;99(49):2502–10, 2511). The first cases of percutaneous transluminal angioplasty of coronary arteries (PTCA) in humans were reported by Gruentzig et al in 1978 (Percutaneous transluminal dilatation of chronic coronary stenosis; First experiences, Schweiz Med Wochenschr Nov. 4, 1978;108(44):1721–3). (See also Gruentzig et al, U.S. Pat. No. 4,195,637, Catheter arrangement, method of catheterization, and method of manufacturing a dilatation element.) The use of a self-expanding vascular stent or endovascular prosthesis to prevent acute reclosure after coronary angioplasty in humans was reported by Sigwart et al. in 1987 (Intravascular stents to prevent occlusion and restenosis after transluminal angioplasty; N Engl J Med Mar. 19, 1987;316(12):701–6). The first angioplasty of the carotid artery in humans was reported by Kerber et al in 1980 (Catheter dilatation of proximal carotid stenosis during distal bifurcation endarterectomy; Am J Neuroradiol 1980; 1:348–9). Multiple centers reported results for stent-supported angioplasty of the carotid artery beginning in 1996 (Yadav et al, Angioplasty and stenting for restenosis after carotid endarterectomy. Initial experience. Stroke 1996;27: 2075–2079; Wholey et al, Percutaneous transluminal angioplasty and stents in the treatment of extracranial circulation. J Invasive Cardiol 1996;9:225–31; Dorros, Carotid arterial obliterative disease: Should endovascular revascularization (stent supported angioplasty) today supplant carotid endarterectomy. J Intervent Cardiol 1996;9:193–196; Bergeron et al, Recurrent carotid disease: will stents be an alternative to surgery? J Endovasc Surg 1996;3:76–9; 21; Amor et al, Endovascular treatment of atherosclerotic internal carotid artery stenosis. J Endovasc Surg 1997;4(Suppl 1):1–14.)

Despite this tremendous progress, problems and difficulties remain in the treatment of carotid artery disease by angioplasty and stenting. In particular, the manipulation of catheters in the carotid arteries can dislodge embolic materials, such as thrombotic material and atherosclerotic plaque, which have the potential of being carried distally by the bloodstream into the cerebral vasculature and causing ischemic damage in the brain. (Naylor et al, Randomized study of carotid angioplasty and stenting versus carotid endarterectomy: a stopped trial. J Vasc Surg 1998;28:326–34; DeMonte et al, Carotid transluminal angioplasty with evidence of distal embolisation. J Neurosurg 1989;70:138–41.)

Methods and devices for embolic protection have been devised to reduce the potential risks of embolization and ischemic damage during carotid angioplasty (Theron et al, New triple coaxial catheter system for carotid angioplasty with cerebral protection. AJNR 1990; 11: 869–874) and during carotid stenting (Theron et al, Carotid artery stenosis: treatment with protected balloon angioplasty and stent placement. Radiology. December 1996;201(3):627–36). (See also Theron, U.S. Pat. No. 5,423,742, Method for the widening of strictures in vessels carrying body fluid, and Theron, U.S. Pat. No. 6,156,005 Ballon catheter for stent implantation. The disclosures of these and all patents and patent applications referred to herein are incorporated by reference.) Distal embolic protection devices currently available for use in performing protected angioplasty and stenting of carotid arteries include filter devices to capture potential emboli and occlusion balloon catheters combined with aspiration to remove potential emboli. The commercially available systems tend to be costly and somewhat cumbersome to use. Another disadvantage of using distal embolic protection devices is that placement of the device distal to the treatment site tends to cause a spasm of the distal cervical internal carotid artery, which can sometimes lead to serious complications. Other approaches, such as retrograde blood flow or proximal occlusion of the carotid artery, have not yet been shown to be effective at reducing embolic complications. What is desired therefore is a simple and effective method of performing protected angioplasty and stenting of carotid arteries that effectively reduces embolic complications and which is free from complications due to spasm of the distal cervical internal carotid artery.

SUMMARY OF THE INVENTION

In keeping with the foregoing discussion, the present invention provides a method of performing angioplasty and stenting that utilizes an embolic protection device combined with aspiration to capture and remove any potential embolic debris. The embolic protection device is deployed within the treatment area, rather than downstream or distal to the treatment site, to avoid any complications due to spasm of the vessel distal to the treatment site. The method is particularly applicable to the treatment of vascular disease at a carotid bifurcation.

Among the three standard technical steps in the technique of carotid angioplasty and stenting, (A) prestenting angioplasty, (B) deployment of the stent, and (C) poststenting angioplasty, the most dangerous, by far, is the poststenting angioplasty step in terms of the embolic risk from detachment of cholesterol particles in the cerebral circulation. We have reported results from a series of patients confirming this and we routinely use cerebral protection only at the poststenting angioplasty step without any complication. The technical evolution in stent devices has made this possibility even more favorable because the lower profile and flexibility of most new stents allows them to be positioned without performing a prestenting angioplasty in most cases.

In the new method, the embolic protection device is deployed only after initial stent placement, with the occlusion balloon inflated within the lumen of the deployed stent, rather than downstream or distally from the stent. This technique has significant advantages over prior methods in that (a) inflation of the occlusion balloon inside the stent provides a full and reliable occlusion of the carotid artery; (b) inflation within the stent provides a more positive fixation of the balloon without migration of the balloon or movement of the balloon during catheter exchanges; (c) the volume to purge is significantly less than with occlusion balloons positioned more distally, which will increase the efficacy of the aspiration of potential embolic particles after angioplasty; and (d) spasm of the distal carotid artery is effectively eliminated.

Another significant step in the new technique is the introduction of the guiding catheter into the lumen of the stent after its deployment. This step provides additional advantages by: (e) simplifying catheter manipulations in the subsequent steps by providing a positive pathway for advancing the catheters into the lumen of the stent; and (f) further reducing the volume that must be purged of potential emboli.

These and other advantages will be apparent upon reading the following detailed description of the invention.

DETAILED DESCRIPTION OF THE INVENTION

Figure 1:
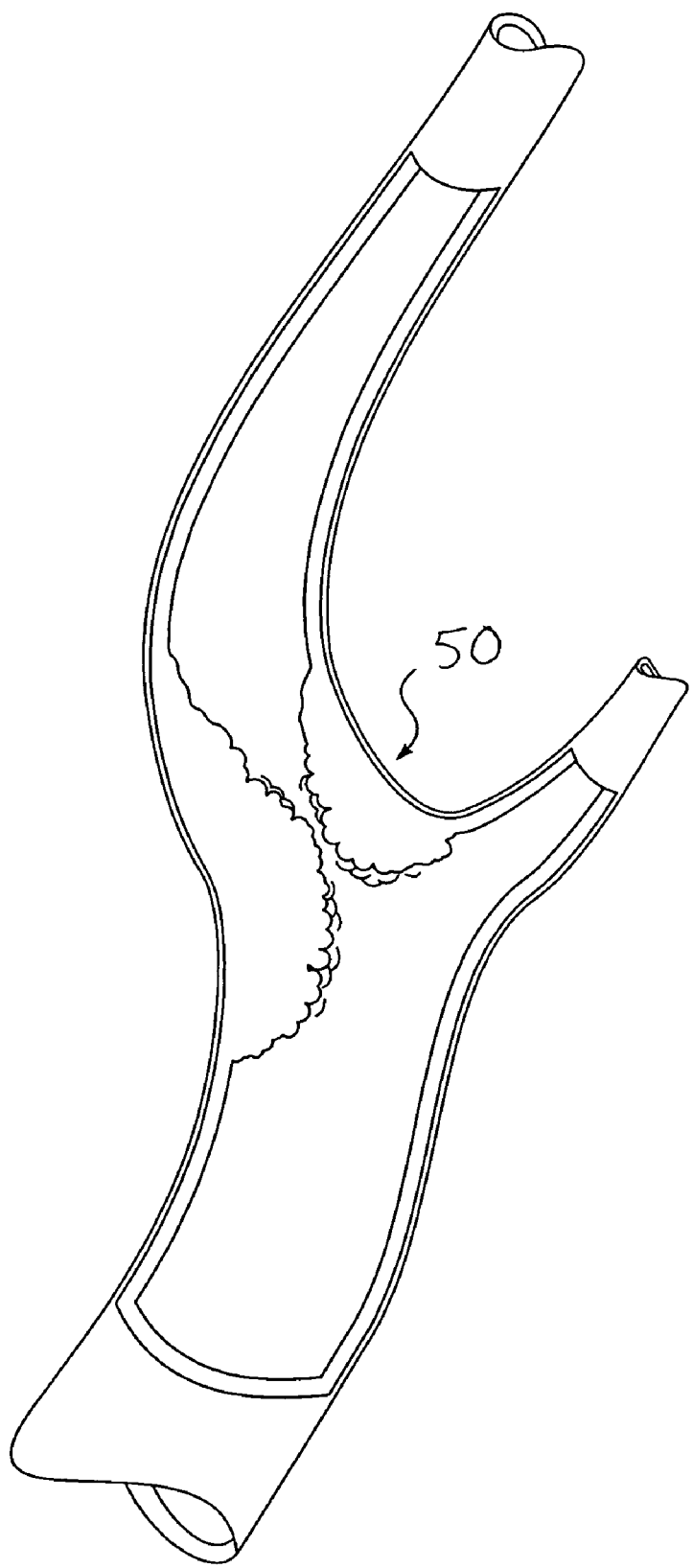
FIG. 1 illustrates a patient's carotid arteries with an atherosclerotic plaque at the carotid bifurcation.

FIG. 1 illustrates a patient's carotid arteries with an atherosclerotic plaque 50 at the carotid bifurcation. The carotid bifurcation is a unique anatomical spot of the human body because of the carotid sinus. This dilatation at the origin of the internal carotid artery and the external carotid artery creates an area of turbulent flow that represents a kind of filter for the cerebral vasculature: the particles of cholesterol that circulate in the artery deposit on the arterial wall, mainly the posterior wall. There is usually no deposit of cholesterol above the site of the bifurcation. One of the goals of the present invention is to concentrate the whole procedure on the actual pathological area, which is limited in length and volume.

The procedure begins by establishing arterial access, typically with a needle puncture of the femoral artery or radial artery. A 7 or 8 French introducer sheath is positioned in the artery at the puncture site using a standard Seldinger technique or other known insertion technique. The common carotid artery is catheterized with a 5 French diagnostic catheter and an exchange guidewire is advanced through the diagnostic catheter into the common carotid artery.

The diagnostic catheter is withdrawn and a 7 or 8 French guiding catheter 52, with a vertebral curve or other suitable distal curve, is advanced over the exchange guidewire into the common carotid artery. The exchange guidewire is withdrawn and angiography is performed by injecting radiopaque dye through the lumen of the guiding catheter 52.

Figure 2:
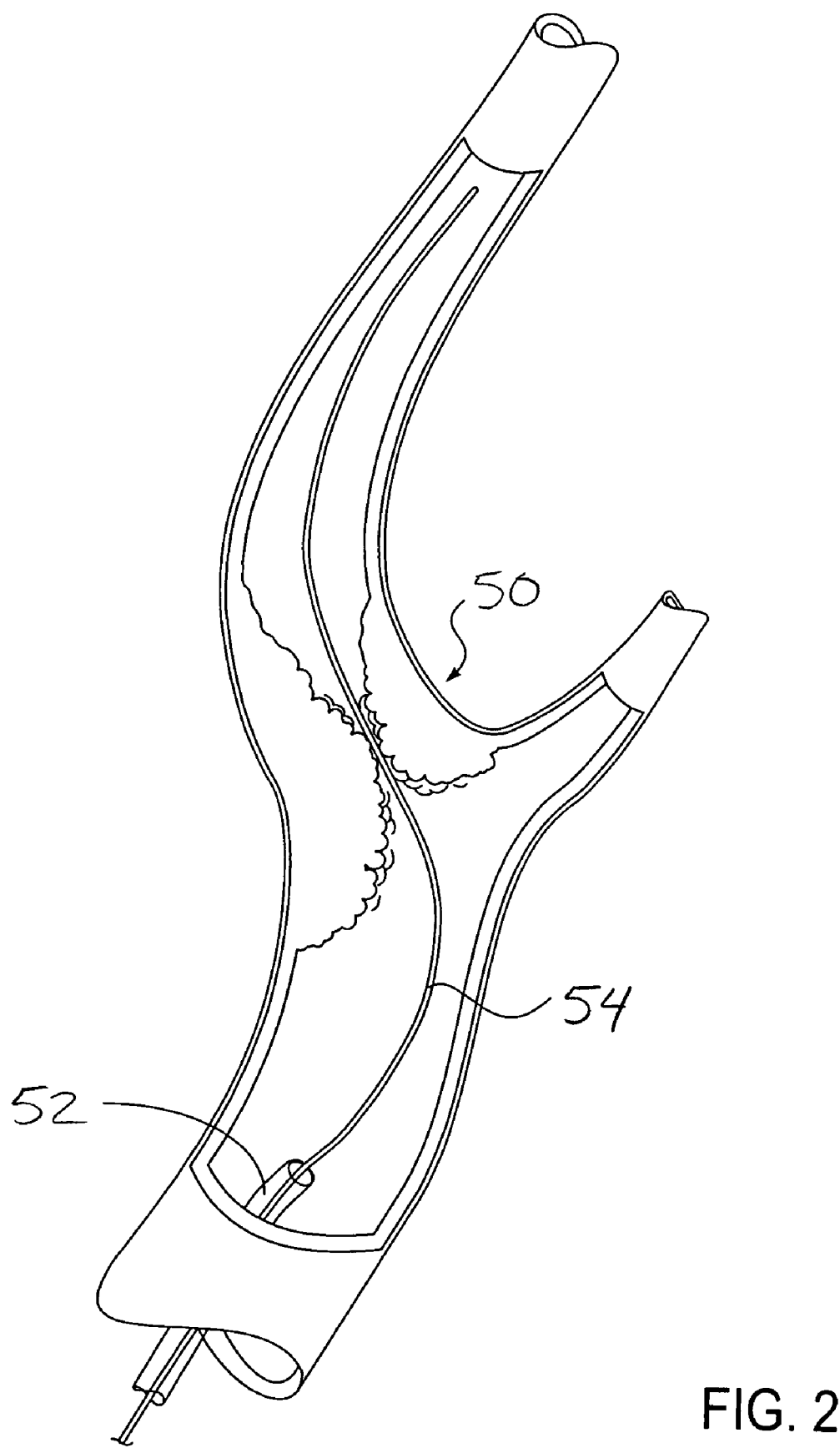
FIG. 2 shows a guiding catheter positioned in the patient's common carotid artery and a guidewire advanced across the stenosis.

Next, a guidewire 54 is advanced through the guiding catheter 52 and across the stenosis 50 in the carotid artery. FIG. 2 shows a guiding catheter 52 positioned in the patient's common carotid artery and a guidewire 54 advanced across the stenosis. Preferably, a coronary style steerable guidewire with a diameter of 0.014 to 0.018 inches is used. Alternatively, the catheter system can be modified to use other diameters of guidewire such as 0.035 to 0.038 inches.

Figure 3:
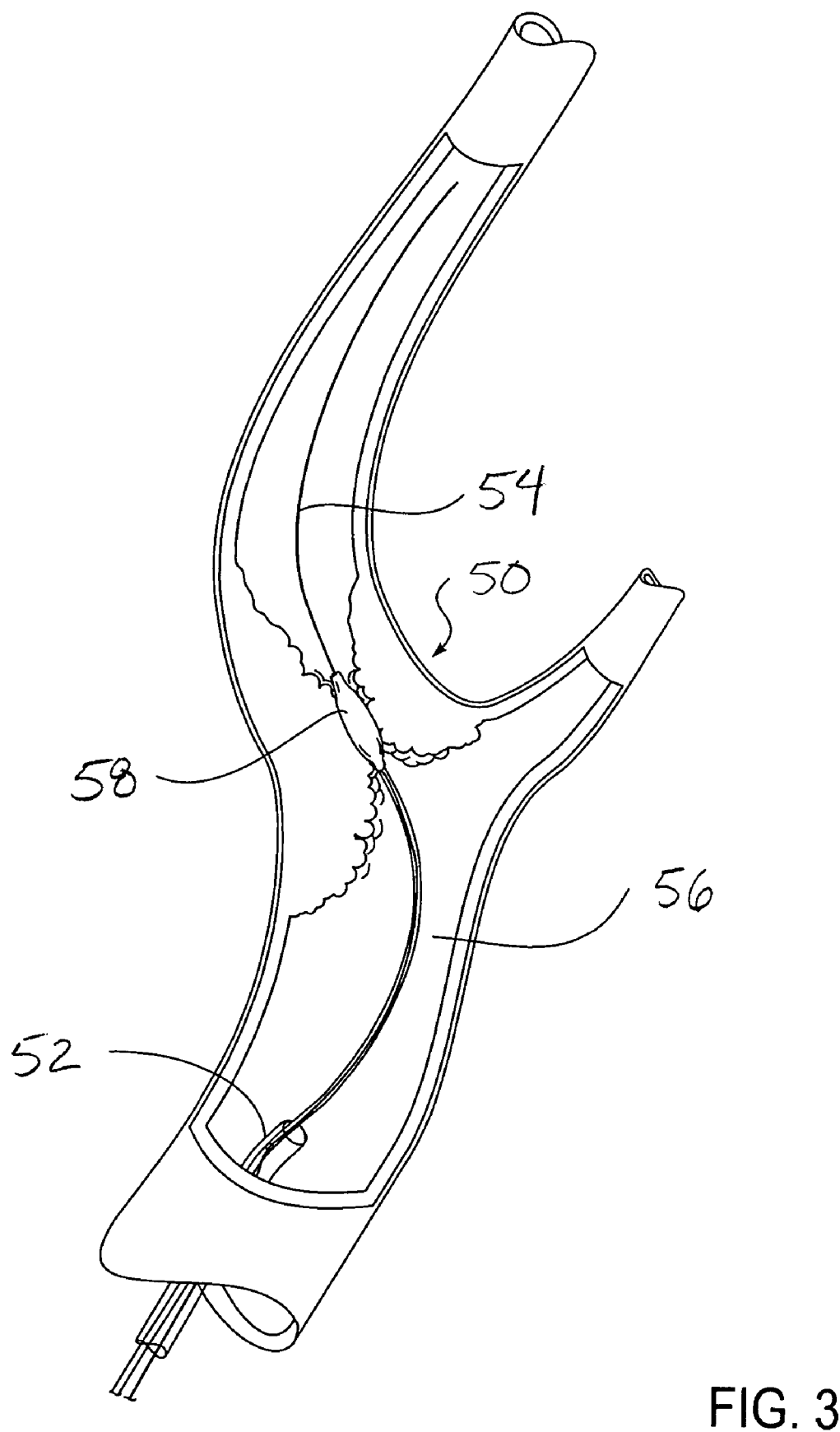
FIG. 3 illustrates the optional step of dilating the stenosis prior to stenting with a small diameter angioplasty balloon.

When necessary (in less than 5% of the cases), a prestenting angioplasty (typically using a rapid exchange style angioplasty catheter 56 with a 2 mm diameter dilatation balloon 58) is performed without embolic protection to facilitate stent crossing. Recent experience has shown that this step is usually unnecessary because recent advances in stent technology have resulted in lower profile, more flexible stents that can cross most lesions without predilatation. FIG. 3 illustrates this optional step of dilating the stenosis prior to stenting. After the stenosis has been dilated, the balloon 58 is deflated and the angioplasty catheter 56 is withdrawn.

Figure 4:
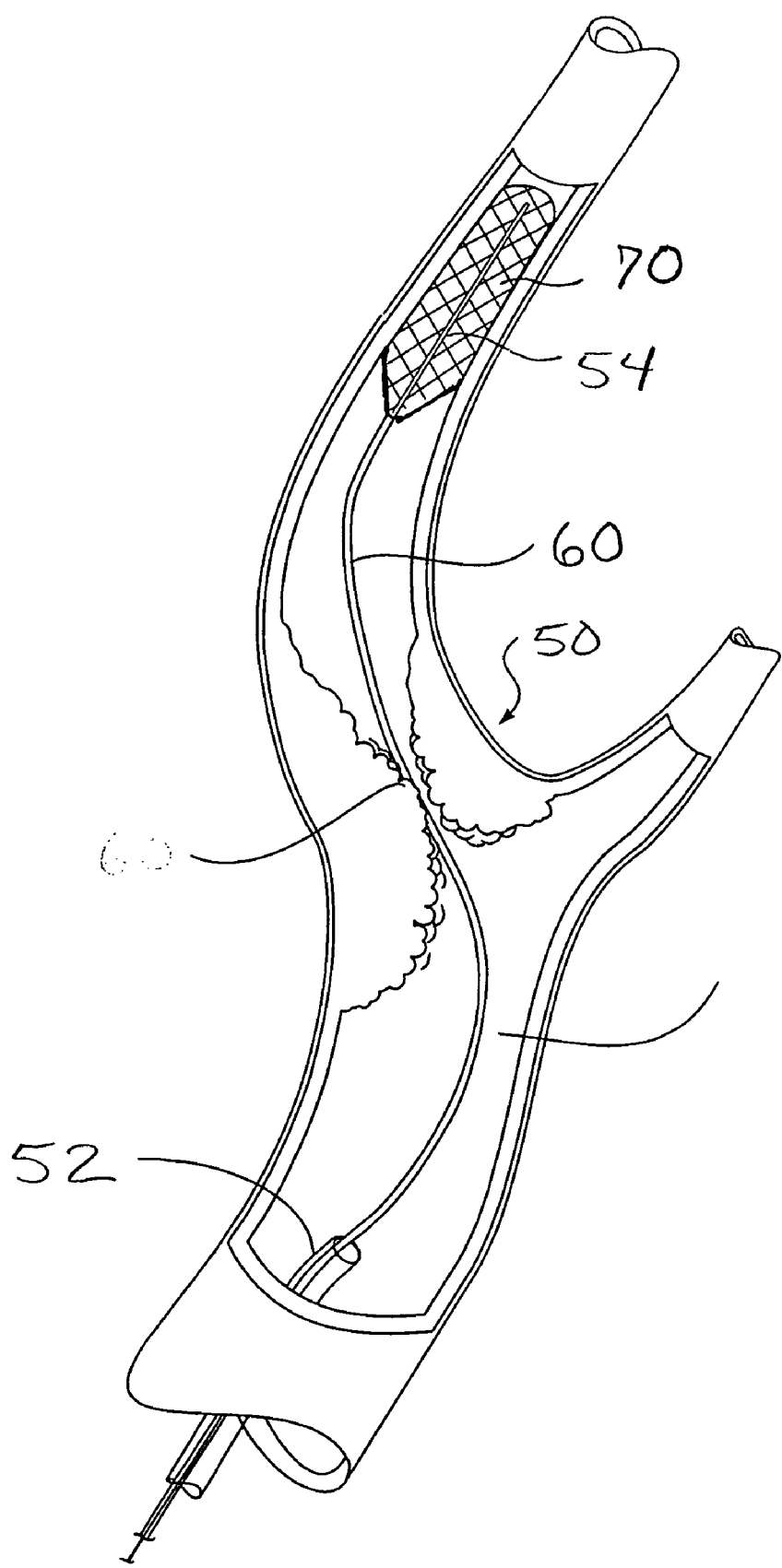
FIG. 4 shows a stent delivery catheter advanced across the stenosis and deploying a self-expanding stent within the lesion.

FIG. 4 shows a stent delivery catheter 60 advanced across the stenosis 50 and deploying a self-expanding stent 70 within the lesion. The stent 70 is deployed without embolic protection as this step presents very low risk for release of embolic material.

In our experience, it is very important to cover the whole atherosclerotic plaque with the stent from a normal arterial wall to a normal arterial wall. This implies the use of long stents. Because of the strong flow in the carotid artery there is no evidence, contrary to the experience in other arteries, that a long stent produces more restenosis than short stents at the carotid bifurcation.

The recommended characteristics of the stent 50 for use in carotid bifurcations are: (a) the stent should be self-expanding, (b) preferably a minimum of 5 cm length should be used, (c) an expanded diameter of 7 to 9 mm is typically necessary to fit with the common carotid artery, (d) a good radial expansion force is mandatory to rule out secondary complications due to aggregation on poorly deployed stents, (e) continuous, not segmented, framework of the stent is recommended to get a straightening of the carotid artery that facilitates the stenting technique, (f) longer and conic stents might be considered in the future. These characteristics may be varied for adapting the stenting technique to other parts of the vasculature.

Figure 5:
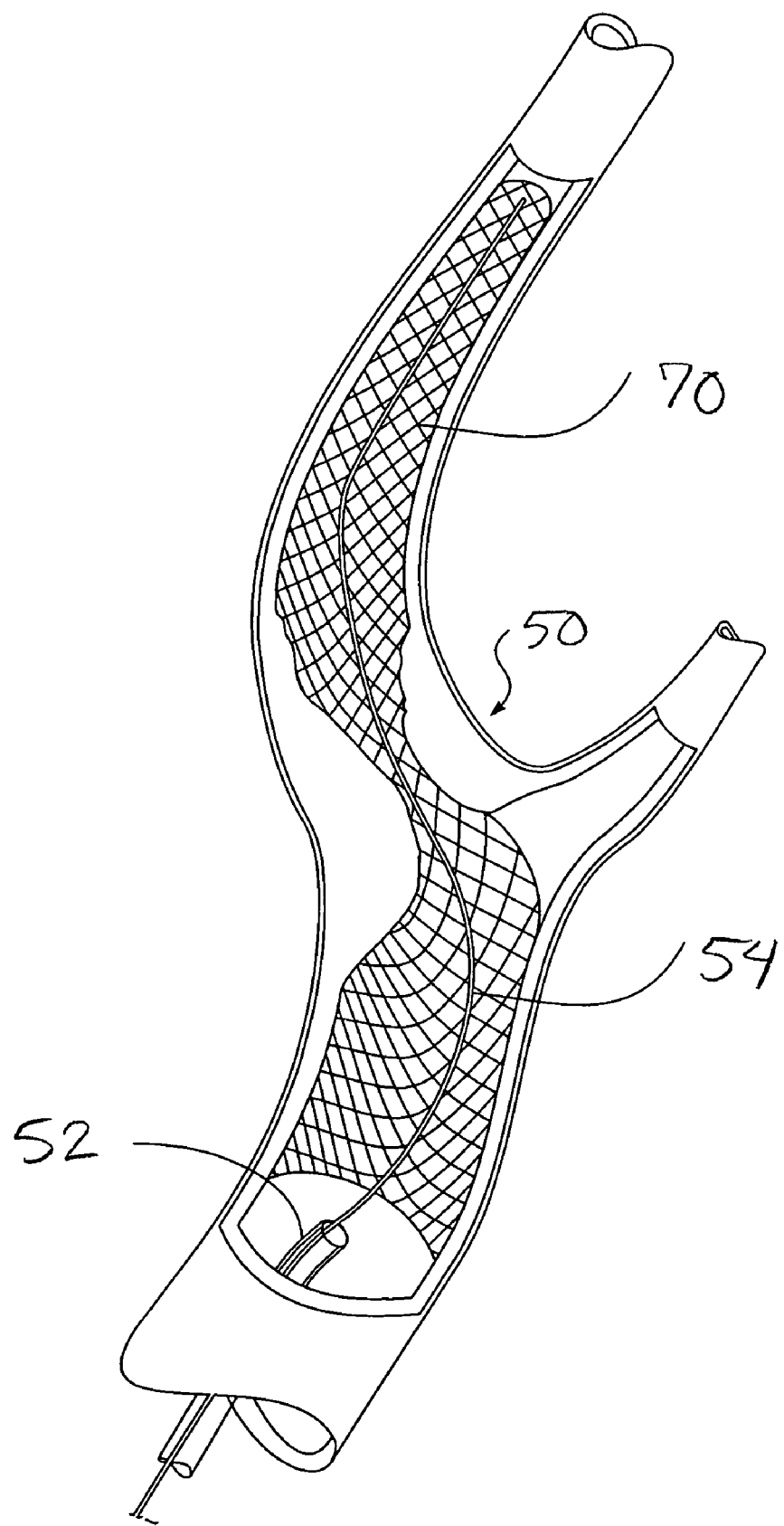
FIG. 5 illustrates the self-expanding stent deployed within the lesion.

FIG. 5 illustrates the self-expanding stent 70 deployed within the lesion. A residual stenosis 50 may remain at the site of the original stenosis, but the entire length of the lesion is effectively covered by the expanded stent 70.

Figure 6:
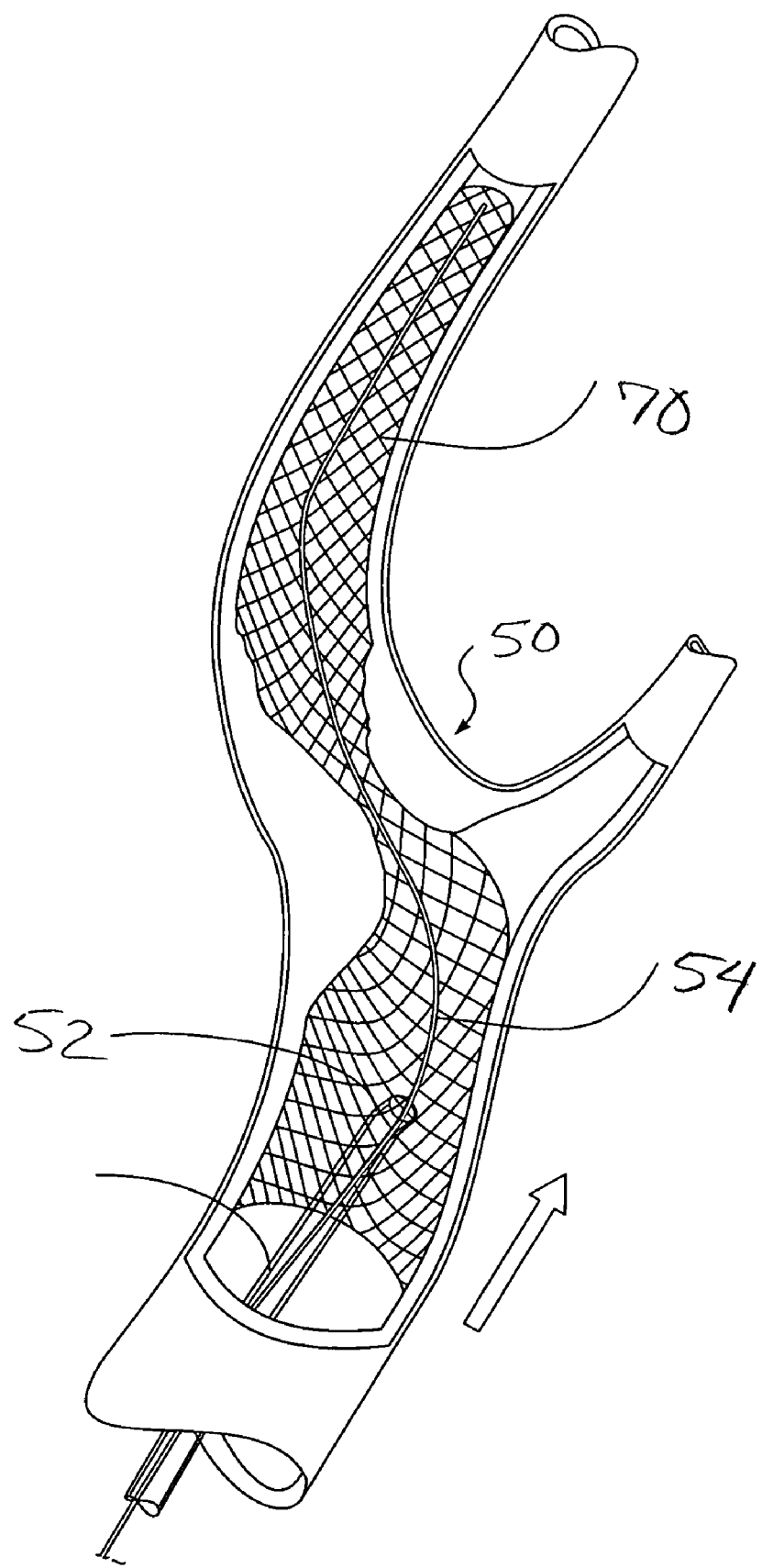
FIG. 6 shows the distal end of the guiding catheter advanced into the lumen of the deployed self-expanding stent.

FIG. 6 shows the distal end of the guiding catheter 52 advanced into the lumen of the deployed self-expanding stent 70.

Figure 7:
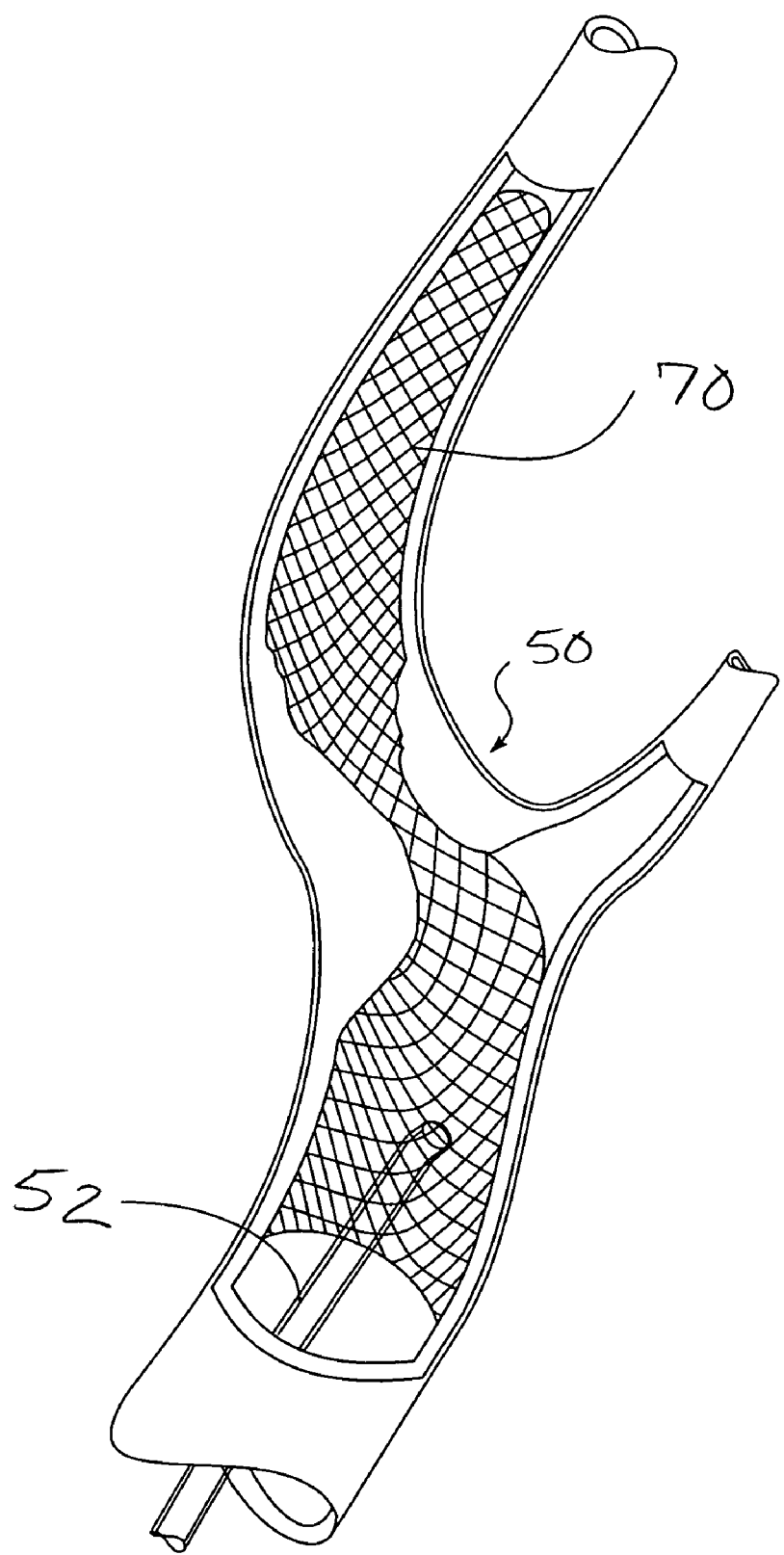
FIG. 7 shows the guiding catheter with the guidewire withdrawn.

FIG. 7 shows the guiding catheter 52 with the guidewire withdrawn. The guiding catheter 52 is firmly positioned into the lumen of the deployed self-expanding stent 70 leaving an open road for the following steps of the technique.

Figure 8:
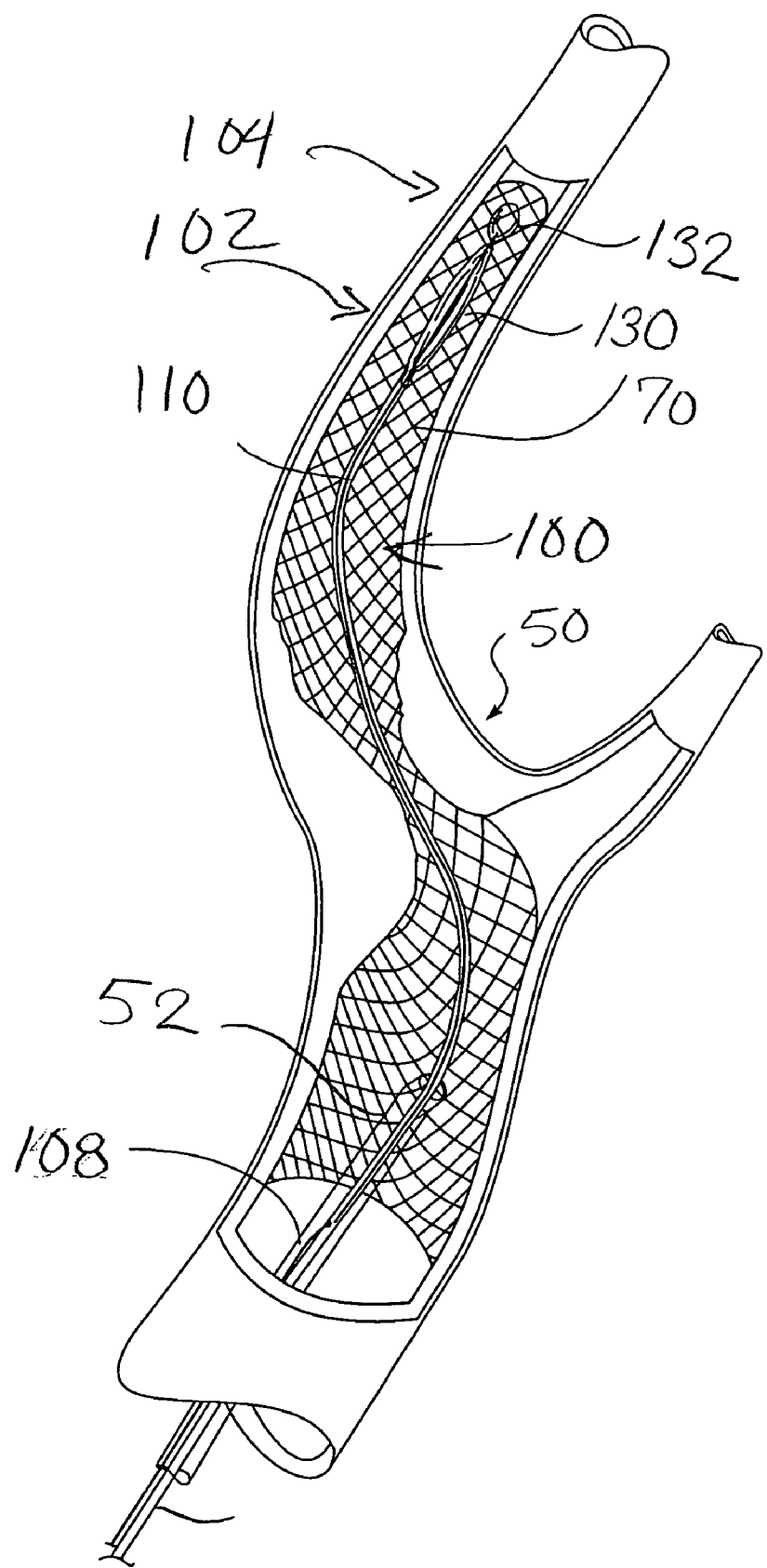
FIG. 8 shows a rapid exchange balloon angioplasty catheter with an occlusion balloon catheter positioned through the guidewire lumen being advanced together through the guiding catheter.

FIG. 8 shows a catheter system 100 that includes a rapid exchange balloon angioplasty catheter 102 with an occlusion balloon catheter 104 positioned through the guidewire lumen 110 being advanced together through the guiding catheter 52. The angioplasty catheter 102 and the occlusion balloon catheter 104 are effectively coupled together and are advanced together as a unit into the guiding catheter 52 and then up to the distal extremity of the stent 70. The rapid exchange balloon angioplasty catheter 102, which is intended for post stenting angioplasty, will typically have a 6 to 9 mm diameter dilatation balloon 130.

The occlusion balloon catheter 104 has an occlusion balloon 132 made of latex, silicone, polyurethane or another material, with a 6 to 9 mm inflated diameter, attached or glued on a simple metallic tube 108 (e.g. superelastic Nitinol or spring temper stainless steel tubing) with a diameter of 0.014 to 0.018 inches and a length that is preferably approximately 120–140 cm or longer. The short length of the tube 108 is possible because of the short guidewire lumen 110 on the rapid exchange or monorail-type angioplasty catheter 102. The elimination of the dead space in the occlusion balloon catheter 104 before the procedure will be performed by aspiration using a simple 3 way stopcock and a 50 cc syringe.

The occlusion balloon catheter 104 will preferably be made with a luer lock fitting permanently attached to the proximal end of the tubing 108, for example by insert molding or gluing the fitting onto the tubing. Alternatively, a removable fitting, such as a Touhy-Borst adapter or a compression fitting, may be used to facilitate catheter exchanges over the tubing 108 of the occlusion balloon catheter 104. In this case, an internal sealing member, such as described in U.S. Pat. No. 6,156,005, may be used to maintain the occlusion balloon 132 in the inflated state when the fitting is removed.

Preferably, the occlusion balloon 132 has a deflated profile that is small enough to fit through the guidewire lumen 110 of the angioplasty catheter 102 for assembly of the catheter system 100. Alternatively, the catheter system 100 can be assembled by inserting the bare tubular shaft 108 of the occlusion balloon catheter 104 through the guidewire lumen 110 of the angioplasty catheter 102 in an anterograde or retrograde fashion and then attaching the occlusion balloon 132 and/or the proximal fitting to the tubular shaft 108. If a permanently attached proximal fitting is used, the two catheters 102, 104 will be permanently coupled together.

The tubular shaft 108 of the occlusion balloon catheter described with a diameter of 0.014 to 0.018 inches could alternatively be made in other diameters, such as 0.035 to 0.038 inches. The rapid exchange angioplasty catheter 102 would have to be modified with a guidewire lumen 110 corresponding to the diameter of the shaft 108 of the occlusion balloon catheter 104. The positioning of the guiding catheter 52 inside of the stent 70 leaves an open avenue that could be used with other instruments (angioplasty, echography, fibroscopy, etc.) as long as they fit into it. These various instruments could be used to perform diagnostic or therapeutic procedures that require isolation of the carotid bifurcation space.

Figure 9:
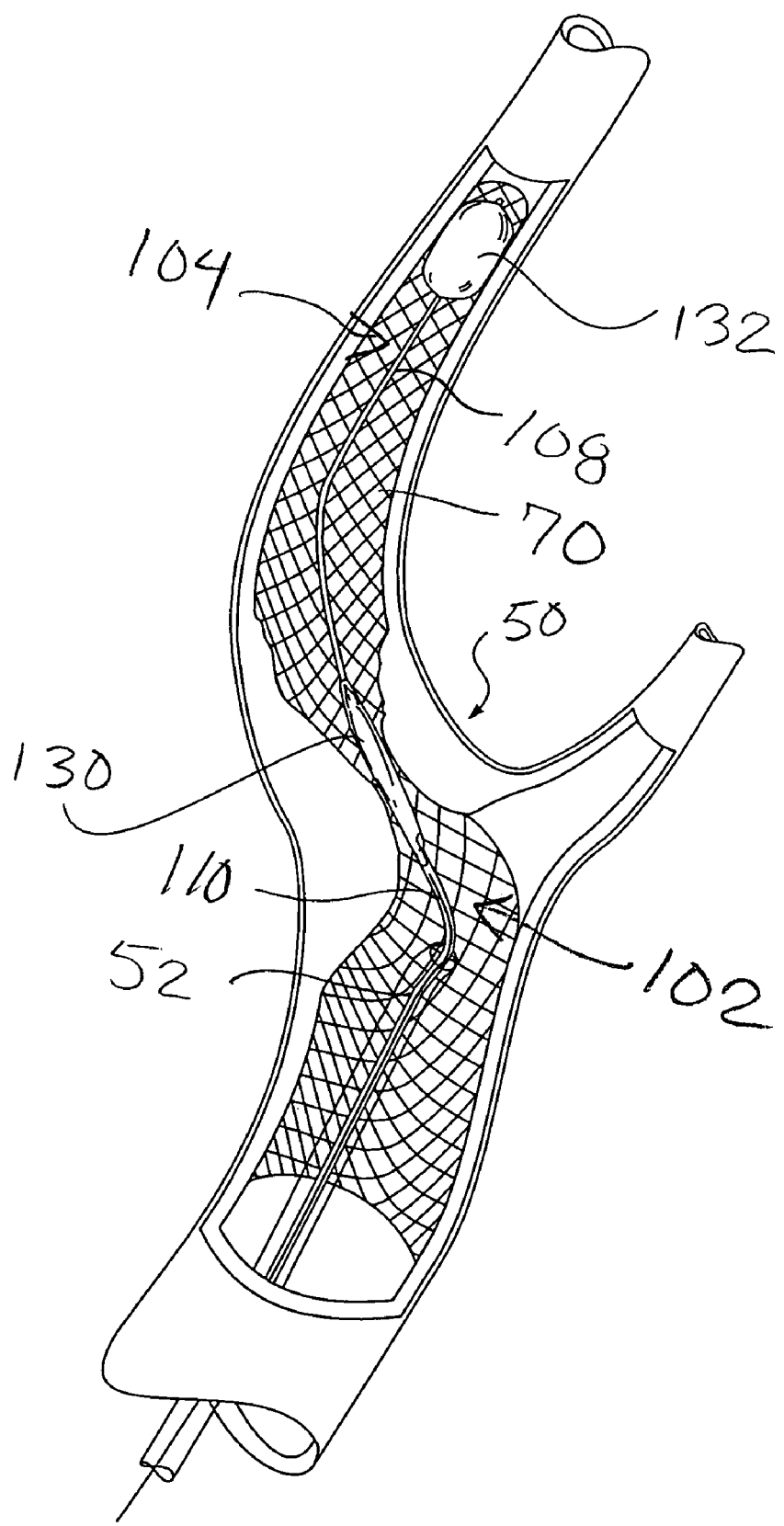
FIG. 9 shows the occlusion balloon inflated within the lumen of the self-expanding stent and the angioplasty catheter positioned with dilatation balloon across the lesion.

FIG. 9 shows the occlusion balloon 132 inflated within the lumen of the self-expanding stent 70 and the angioplasty catheter 102 positioned with dilatation balloon 130 across the lesion 50. The occlusion balloon 132 is inflated in the distal part of the stent 70 to occlude the carotid artery and to prevent any embolic debris from traveling downstream from the treatment site. Then, the angioplasty balloon 130 is withdrawn to the site of the remaining narrowing of the stent 70 to be dilated.

Figure 10:
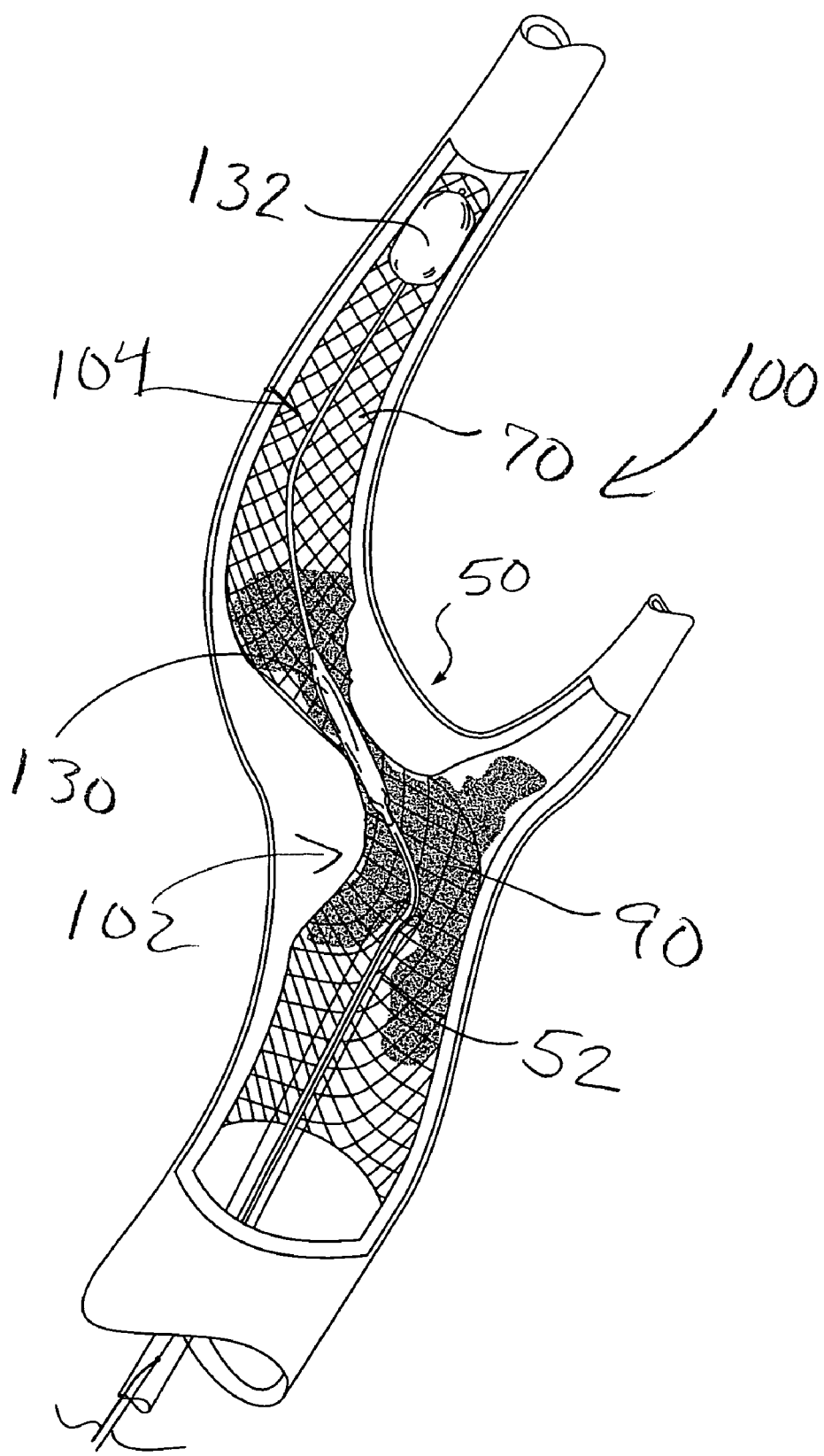
FIG. 10 shows an angiography study performed to confirm occlusion of the internal carotid artery prior to dilatation of the lesion.

FIG. 10 shows an angiography study performed to confirm occlusion of the internal carotid artery prior to dilatation of the lesion 50. The patient is clinically tested. An angiography series is performed to confirm the effective temporary occlusion of the internal carotid. The contrast 90 should remain close to the bifurcation site and usually does not reach the occlusion balloon 132.

Figure 11:
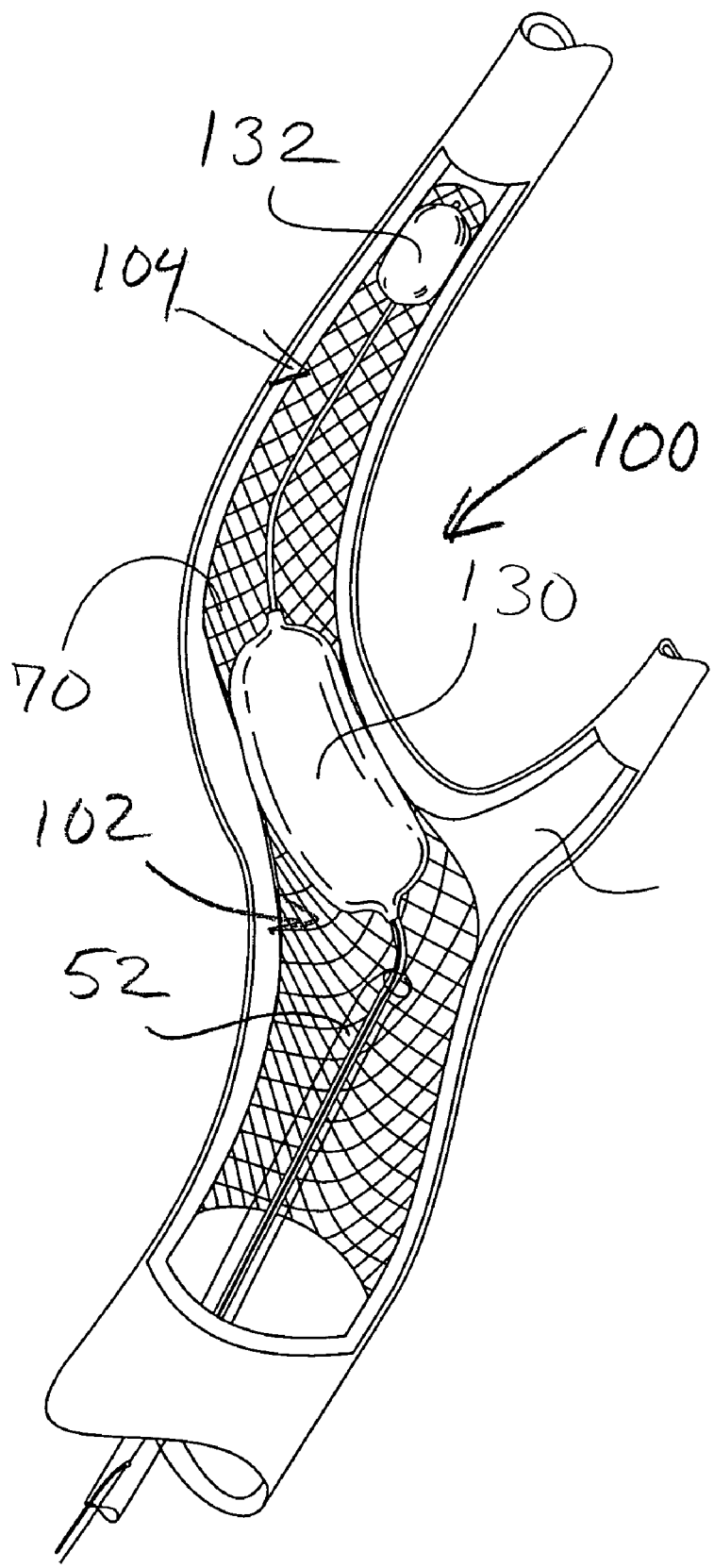
FIG. 11 shows the angioplasty balloon inflated to dilate the stenosis and complete the deployment of the self-expanding stent.

FIG. 11 shows the angioplasty balloon 130 inflated to dilate the stenosis 50 and to complete the deployment or expansion of the self-expanding stent 70. It is recommended that atropine be injected at least 5 minutes previously to rule out the bradycardia induced by the compression of the carotid glomus.

After completion of the poststenting angioplasty, the angioplasty balloon 130 is deflated and the angioplasty catheter is withdrawn from the guiding catheter 152. The tubular shaft 108 of the occlusion balloon catheter 104 has sufficient length that the short guidewire lumen 110 of the angioplasty catheter can be "parked" on the shaft 108 near the proximal end of the occlusion balloon catheter 104 so that it will not interfere with the aspiration step, which is to follow. Alternatively, if the occlusion balloon catheter 104 is made with a removable proximal fitting, the fitting may be removed at this point so that the angioplasty catheter 102 can be removed completely. The internal sealing member described above will maintain the occlusion balloon 132 in the inflated state.

Figure 12:
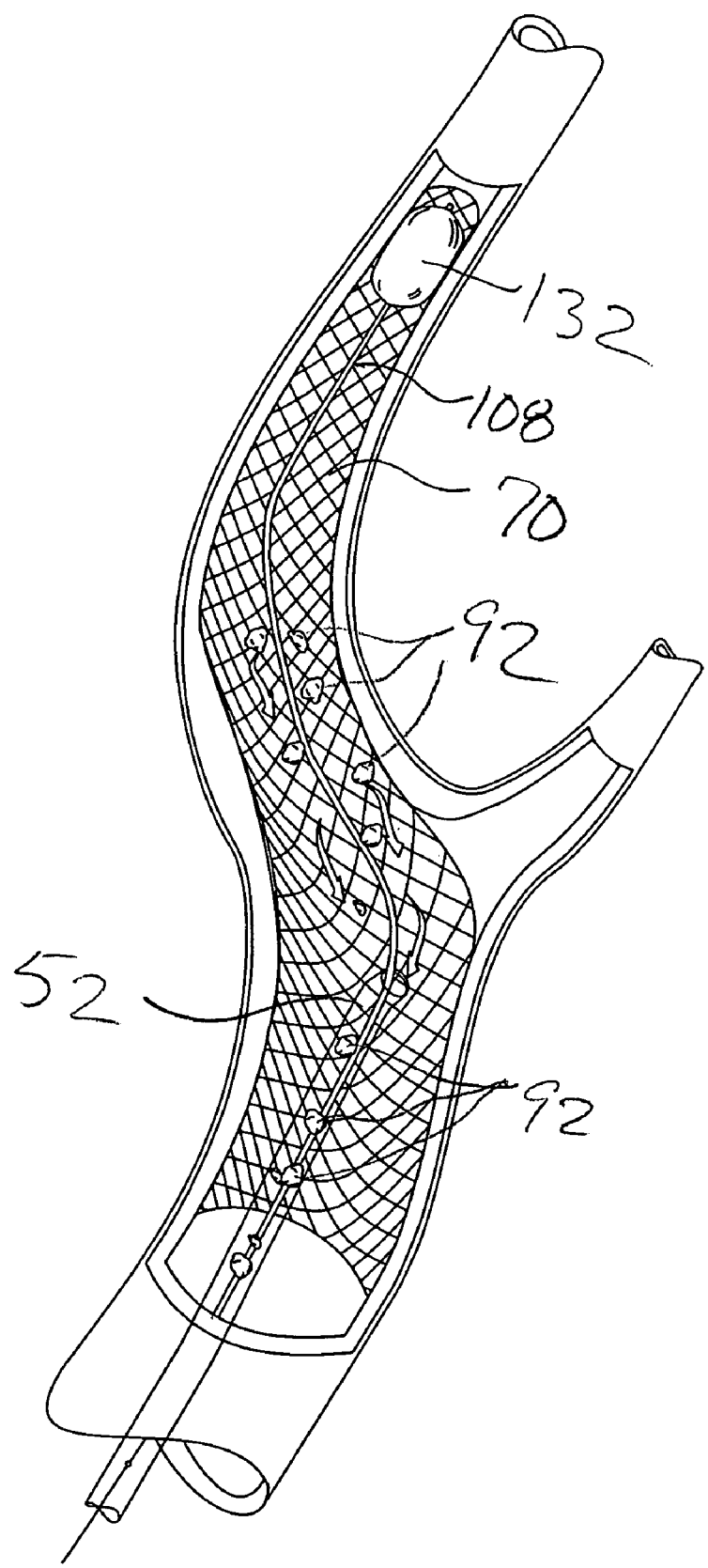
FIG. 12 illustrates potential embolic material being aspirated through the lumen of the guiding catheter.

With the occlusion balloon 132 still inflated, blood is aspirated back through the lumen of the guiding catheter 52. FIG. 12 illustrates potential embolic material 92 being aspirated through the lumen of the guiding catheter 52.

The occlusion balloon 132 is then deflated and the angioplasty catheter 102 and occlusion balloon catheter 104 are withdrawn. An angiography series is performed through the guiding catheter 52 to verify patency of the lumen and full deployment of the self-expanding stent 70. Then, the guiding catheter 52 and introducer are withdrawn and the puncture site is closed.

Figure 13:
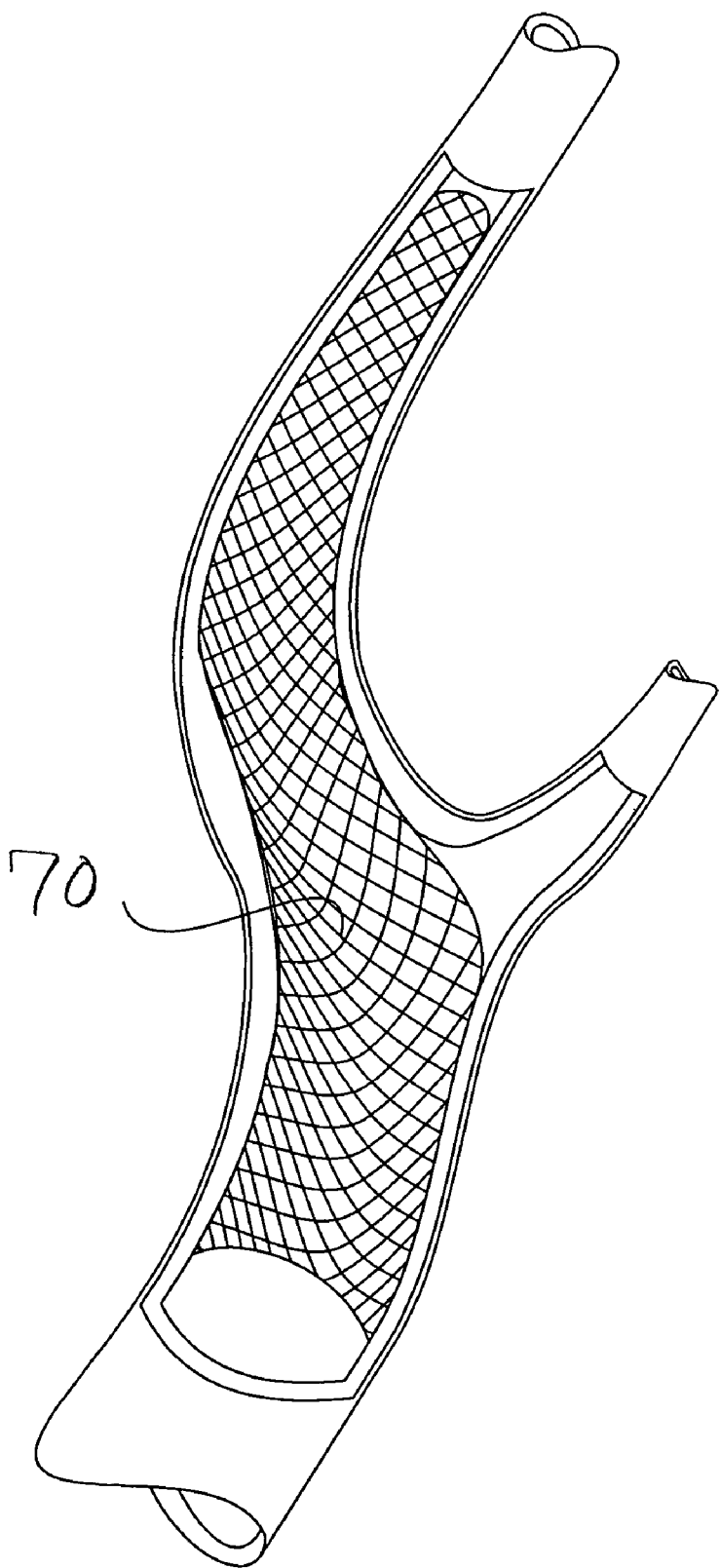
FIG. 13 illustrates the patient's carotid bifurcation after completion of the protected angioplasty and stenting procedure.

FIG. 13 illustrates the patient's carotid bifurcation with the fully deployed stent 70 after completion of the protected angioplasty and stenting procedure.

Although it has been described in relation to treatment of obstructive carotid artery disease, the method of the present invention can be adapted for performing protected angioplasty and stenting in other parts of the vasculature, for example in the coronary arteries.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. A method of treating vascular disease, comprising:
positioning guiding catheter;
deploying a stent within a blood vessel of a patient;

advance guiding catheter within the lumen of the deployed stent;

positioning an embolic protection device within a lumen of the deployed stent;

deploying the embolic protection device within the lumen of the deployed stent;

introducing a dilatation catheter into the lumen of the deployed stent;

inflating a dilatation balloon mounted on the dilatation catheter to dilate a portion of the stent at a location proximally from the deployed embolic protection device;

deflating the dilatation balloon and withdrawing the dilatation catheter from the lumen of the stent;

aspirating blood and potential emboli through a lumen of an aspiration catheter placed within the lumen of the deployed stent;

undeploying the embolic protection device and withdrawing the embolic protection device and the aspiration catheter from the lumen of the stent.

2. The method of claim 1, wherein the embolic protection device comprises a catheter with an inflatable occlusion balloon mounted near a distal end of the catheter, and wherein deploying the embolic protection device comprises inflating the occlusion balloon within the deployed stent to occlude the lumen of the stent.

3. The method of claim 1, wherein the dilatation catheter is a rapid exchange catheter having a guide lumen that extends through a distal portion of the dilatation catheter, and wherein a shaft of the embolic protection device is inserted through the guide lumen.

4. The method of claim 1, wherein the aspiration catheter is a guiding catheter, and wherein the dilatation catheter and the embolic protection device are inserted through the lumen of the guiding catheter.

5. The method of claim 1, wherein the stent is a self-expanding stent, and wherein deploying the stent within a blood vessel of a patient comprises allowing the stent to self-expand within the blood vessel.

6. The method of claim 1, wherein the stent is deployed within a patient's carotid artery.

7. The method of claim 1, wherein the stent is deployed within a patient's carotid bifurcation.

8. The method of claim 1, further comprising predilating the patient's blood vessel prior to deploying the stent within the blood vessel.

9. A method of treating vascular disease, comprising:

deploying a self-expanding stent within a patient's carotid artery;

advancing a distal end of a guiding catheter to a position within the lumen of the deployed stent;

advancing an embolic protection device through a lumen of the guiding catheter into the lumen of the deployed stent;

deploying the embolic protection device by inflating an occlusion balloon mounted near a distal end of the embolic protection device within the lumen of the deployed stent to occlude the lumen of the stent;

introducing a dilatation catheter through the lumen of the guiding catheter and advancing a distal end of the dilatation catheter into the lumen of the deployed stent;

inflating a dilatation balloon mounted on the dilatation catheter to dilate a portion of the stent at a location proximally from the inflated occlusion balloon;

deflating the dilatation balloon and withdrawing the dilatation catheter from the lumen of the stent;

aspirating blood and potential emboli through the lumen of the guiding catheter;

deflating the occlusion balloon and withdrawing the embolic protection device and the guiding catheter from the lumen of the stent.

10. The method of claim 9, wherein the dilatation catheter is a rapid exchange catheter having a guide lumen that extends through a distal portion of the dilatation catheter, and wherein a shaft of the embolic protection device is inserted through the guide lumen.

* * * * *